United States Patent [19]

Wolf et al.

[11] Patent Number: 5,443,855
[45] Date of Patent: Aug. 22, 1995

[54] COSMETICS AND PHARMACEUTICALS CONTAINING EXTENSINS AND RELATED METHODS

[75] Inventors: Barbara Wolf, Scarsdale; Marlene Tietjen, New York, both of N.Y.

[73] Assignee: Revlon Consumer Products Corporation, New York, N.Y.

[21] Appl. No.: 296,385

[22] Filed: Aug. 26, 1994

Related U.S. Application Data

[63] Continuation of Ser. No. 27,996, Mar. 8, 1993, abandoned, which is a continuation-in-part of Ser. No. 933,130, Aug. 21, 1992, abandoned, which is a continuation of Ser. No. 761,574, Sep. 18, 1991, abandoned.

[51] Int. Cl.⁶ .......................... A61K 7/00; A61K 7/02; A61K 7/04; A61K 7/075
[52] U.S. Cl. .......................... 424/401; 424/61; 424/70.14; 424/73; 514/844; 514/845; 514/846; 514/847; 514/881; 514/937; 514/938; 514/944
[58] Field of Search .......................... 424/401, 61, 63, 70, 424/71, 73, 499; 514/2, 8, 844, 847, 944, 937–943, 881, 944

[56] References Cited

U.S. PATENT DOCUMENTS

| | | | |
|---|---|---|---|
| 3,907,580 | 9/1975 | Van Ham | 406/158 |
| 3,964,500 | 6/1976 | Drakoff | 132/7 |
| 4,131,650 | 12/1978 | Braumer | 424/401 |
| 4,420,339 | 12/1983 | Kato | 106/124 |
| 4,451,397 | 5/1984 | Huc | 260/123.7 |
| 4,507,279 | 3/1985 | Okuyame | 424/63 |
| 4,507,279 | 3/1985 | Okuyama | 424/63 |
| 4,591,501 | 5/1986 | Cioca | 424/401 |
| 4,592,907 | 6/1986 | Akimoto | 424/70 |
| 4,826,809 | 5/1989 | Giesen | 514/2 |
| 5,053,220 | 10/1991 | Arraudeau | 424/401 |

FOREIGN PATENT DOCUMENTS

| | | |
|---|---|---|
| 149872A | 7/1985 | European Pat. Off. |
| 3445919 | 6/1986 | Germany . |
| 0116622 | 6/1985 | Japan . |
| 2148714 | 6/1985 | United Kingdom . |

OTHER PUBLICATIONS

Perserpio Cosmetic News II, #3 (1988).
Kieliszewski et al. Plant Physiology (1987) 85, 823–827.
Planta 174(3) (1988) 321–332.
Plant Physiology (1988) 87, 616–621.
Plant Physiology (1990) 92, 316–326.
Phytochemistsry (1986) 25:5, 1021–1030.
Plant Physiology (1988) 86, 848–856.
Phytochemistry (1984) 23:6 1233–1239.
Plant Physiology (1984) 76, 414–417.
Biochimica Et Biophysica Acta 257 (1972) 421–432.

Primary Examiner—Gollamudi S. Kishore
Attorney, Agent, or Firm—Julie Blackburn

[57] ABSTRACT

Cosmetic and pharmaceutical compositions containing effective amounts of substantially intact extensin proteins and the related methods.

17 Claims, 1 Drawing Sheet

NO TREATMENT | TREATED

NO TREATMENT | TREATED

NO TREATMENT | TREATED

COSMETICS AND PHARMACEUTICALS CONTAINING EXTENSINS AND RELATED METHODS

This application is a continuation of U.S. application Ser. No. 08/027,996 filed Mar. 8, 1993, now Abn. which is a continuation in part of U.S. patent application Ser. No. 07/933,130 filed Aug. 21, 1992, now Abn. which is in turn a continuation of U.S. patent application Ser. No. 761,574, filed Sep. 18, 1991, now abandoned.

TECHNICAL FIELD

The invention is in the field of cosmetic and pharmaceutical compositions containing extensin proteins.

BACKGROUND OF THE INVENTION

Cosmetics companies are particularly interested in formulating treatment cosmetics which exert beneficial effects on skin and hair. Since it is known that various animal derived substances provide beneficial effects to skin and hair, it has become popular to incorporate these substances into cosmetics and personal care products. For example, animal collagen is known to have moisturizing and film forming properties, and is a popular additive to treatment cosmetics. Animal collagen protein is the main component of connective tissues, skin, muscles and tendons. It is a fibrous protein of about 100,000 molecular weight, rich in proline and hydroxyproline, and structurally analogous to a three-stranded rope in which each strand is a polypeptide chain. Collagen is responsible for most of skin structure. In the course of aging the polypeptide chains of collagen polymerize The result is "cross linking", which causes wrinkling of the skin as well as reduction in skin elasticity.

Other non-collagen animal proteins such as plasma proteins, placental proteins, or proteins from milk sources are also popular as cosmetics additives, as well as proteins from lower animals such as silkworm, fish, bacteria, yeast, or non-specified marine sources.

Extensins are a family of plant derived hydroxyproline rich glycoproteins (HRGP) firmly bound to the primary cell wall of several species of monocotyledonous and dicotyledenous plants. Extensins are also rich in serine, valine, tyrosine, lysine, and in some instances threonine, and the polypeptide backbone comprises repeating hydroxyproline units in conjunction with other basic amino acids such as valine, lysine, proline, tyrosine, histidine, serine, and threonine. The hydroxyproline component is heavily glycosylated. Extensins play a role in growth, regulation, stress response, cell-cell recognition, and reproductive physiology of plants. The protein is widely distributed throughout the plant kingdom. Extensins are generally insoluble in muro because of their extensive cross linking, so the intact protein has not been isolated from mature plants, which has made the scientific study of intact extensin protein much more difficult. A hydrolyzed form of extensin is available commercially through Centerchem, Stamford, Conn. However, this hydrolyzed product contains very small polypeptide chains having molecular weights of 100–1500 daltons. The term "hydrolyzed" means that the protein has been denatured, possibly fragmented, and the tertiary structure destroyed. It is important to understand that the tertiary structure of a protein is intimately involved with the proper biochemical functioning of that protein.

The estimated size of intact extensin protein is greater than 100,000 daltons, or about 100,000–150,000 daltons. The term "intact" means that the protein is not hydrolyzed or denatured, but still retains its tertiary structure.

It is known that prior to incorporation of insoluble cross linked extensin into the plant cell wall it exists in a soluble form which can be isolated by salt extraction of cell suspension cultures containing the soluble precursor form.

It has unexpectedly been discovered that this soluble form of extensin may be incorporated into cosmetics as an analog for animal collagen and will act to smooth, tighten, and enhance skin texture. Extensins also contain large amounts of humectant sugars which are capable of binding water, thus making them ideal humectants.

SUMMARY OF THE INVENTION

The invention is directed to cosmetic compositions comprising cosmetically effective amounts of substantially intact extensin protein.

The invention is directed to pharmaceutical compositions comprising pharmaceutically effective amounts of substantially intact extensin protein.

The invention is directed to a method of moisturizing and forming a film on skin comprising applying to the skin a cosmetic or pharmaceutical composition containing an effective amount of substantially intact extensin protein.

DETAILED DESCRIPTION

Figure 1:
FIG. 1 shows a scanning electron micrograph of a silicone replica of skin at 25× magnification. About 20 microliters of a 0.2% solution of extensin from carrots was applied to the right half of an area 15 millimeters in diameter (about 44 square millimeters). The left half of the area was left untreated.
Figure 2:
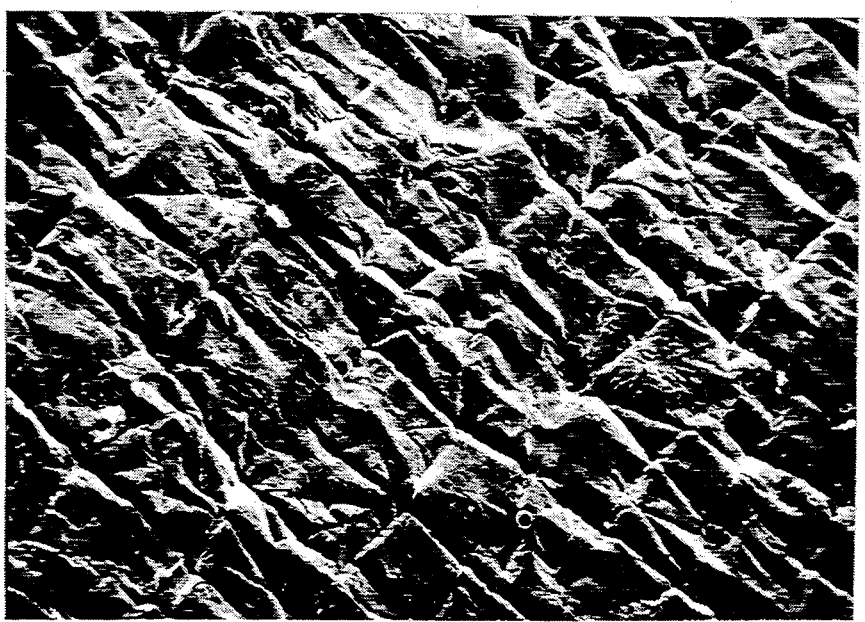
FIG. 2 shows a scanning electron micrograph of a silicone replica of skin at 25× magnification. About 40 microliters of a 0.2% solution of high molecular weight non-extensin protein from wheat was applied to the right half of an area 15 millimeters in diameter (44 square millimeters of treated surface area), while the left half was left untreated. A comparison of both figures reveals that skin treated with extensin protein has an appreciably more intact and visible film than skin treated with high molecular weight non-extensin wheat protein or untreated skin.

The term "substantially intact" generally means the full length extensin of 100,000–150,000 daltons extracted from the plant cell wall and which has retained its tertiary structure, or dimers thereof. The term "substantially intact" also refers to the situation wherein the full length intact extensin of 100,000–150,000 daltons has been "nicked" or cut in several or more pieces which still retain structural integrity and the tertiary configuration of the intact protein, for example, fragments of the intact protein ranging from 2000–149,000 daltons or 10,000–70,000 daltons, or dimers thereof. The term "substantially intact" does not refer to hydrolysates which have lost their tertiary structure through hydrolysis or other means. Hydrolysates are generally of 100–1500 daltons.

The term "extensin" or "extensin protein" means a soluble hydroxyproline-rich glycoprotein analog to animal collagen which is extracted from plant cell walls. Structurally extensins are comprised of a polypeptide backbone comprising repeating hydroxyproline units in conjunction with other basic amino acids such as valine, lysine, proline, tyrosine, histidine, serine, and threonine.

The intact extensin proteins used in the cosmetic compositions of the invention are described in the following publications and may be extracted from various plants by methods described in these publications: *Biochimica Et Biophysica Acta,* Vol. 257(1972) 421–432; *Plant Physiology,* Vol. 76 (1984), 414–417; *Phytochemistry,* Vol 23, No. 6 (1984) 1233–1239; *Plant Physiology* Vol. 85 (1987) 823,827; *Plant Physiology,* Vol. 87 (1987) 616–621; *Plant Physiology,* Vol. 86 (1988) 848–856; *Phytochemistry, Vol.* 25, No. 5 (1986) 1021–1030.

Generally, soluble extensin precursors may be extracted from plant species in the growth phase by salt extraction of crude extensin protein fractions from concentrated plant cell suspension pellets or explant homogenates. Various metallic salt solutions are suitable for this purpose including aluminum chloride, calcium chloride, lapyrium chloride, sodium chloride, etc. The crude extensin protein extracts may then be further purified by acid precipitation of contaminants using acids such as trichloroacetic acid. Extensin proteins are generally soluble in 5–10% trichloroacetic acid. Then standard protein purification methods may be used for further purification, for example size exclusion affinity chromatography or ion exchange chromatography.

A 0.5% solution of extensin generally produces a flexible film that keeps the skin pliable and firm for five to six hours after application. The cosmetic benefits are seen in cosmetic and pharmaceutical compositions as outlined below.

The extensin extracts may be incorporated into a variety of cosmetic and pharmaceutical compositions. Cosmetic or pharmaceutical compositions containing effective amounts of extensins improve texture, smoothness, and moisture content of the skin.

The term "cosmetic composition" means a composition applied externally to skin, nails, or hair of the human body, for purposes of beautifying, coloring, conditioning, or protecting the bodily surface. Examples of cosmetic compositions in accordance with the invention include lotions, creams, moisturizers, gels, sun screens, makeup, cleansers, shampoos, hair conditioners, skin firming compositions, protein concentrates, after shaves, eyeshadows, blushes, nail enamels and so on.

The term "pharmaceutical composition" means a composition applied externally to the skin, hair, or nails of the human body for therapeutic purposes. Examples of pharmaceutical compositions in accordance with the invention include ointments, creams, lotions, gels, solutions, and so on.

The invention comprises cosmetic compositions comprising a cosmetically effective amount of extensin protein. A cosmetically effective amount of extensin protein in accordance with the invention is about 0.001–30% by weight of the total composition, with 0.1–10% preferred, and 0.5–5% most preferred.

The extensin proteins may be incorporated into a wide variety of cosmetic compositions. For example, cosmetically effective amounts of extensin may be incorporated into moisturizing lotions for application to human facial or body skin. These lotions generally contain from about 20–80% oil and 10–80% water in an emulsion form. In addition the moisturizing lotion may contain humectants, emollients, surfactants, fragrances, preservatives, and so forth. About 5–10% humectant, about 5–20% emollient, and about 0.5–10% surfactant are suggested.

Extensins may be easily incorporated into moisturizing creams. Creams generally contain from about 20–70% water and about 30–70% oil. In addition, creams may contain a variety of humectants, emollients, surfactants, preservatives, and fragrances. About 5–10% humectant, about 5–20% emollient, and about 0.5–10% surfactant are suggested.

Extensins may also be incorporated into treatment makeups. Generally makeup formulations comprising 5–70% oil, 10–95% water, and about 5–40% pigment are suitable. In addition the makeup may contain surfactants, silicone, humectants, emollients, preservatives, fragrances, etc. Generally 0.5–10% surfactant, 0.1–30% silicone, 5–10% humectant, 0.1–30% emollient, and 0.1–5% preservative is suggested.

Extensins may also be incorporated into colored cosmetics such as eyeshadow or blush. For example, a suitable eyeshadow comprises 5–40% pigments, 1–50% oil, and 1–20% waxes. Additionally the composition may contain one or more of 10–60% water, 0.5–30% surfactant, 1–10% humectants, 0.1–5% preservative, and 0.1–20% silicone.

Extensins are also suitable for incorporation into shampoos and hair conditioners. Suitable shampoo formulations include 1–40% surfactant and 10–90% water. Suitable hair conditioning formulations include 30–95% water, 0.5–30% conditioning ingredients such as emollients, proteins, shine enhancers, and so forth, and 1–40% surfactant. Hair conditioners and shampoos may also contain thickeners and silicone. About 0.05–15% silicone is suggested in shampoos and hair conditioners.

Extensins may also be incorporated into cleansers, aftershaves, toners, fragrance splashes, and even nail treatment products or nail enamels. For example, fragrance splashes, aftershaves and toners, generally comprise about 10–70% alcohol. In addition, 0.01–5% surfactant may be added as well as 1–5% humectants, and up to 25% perfume.

Extensins may be incorporated into traditional nail enamels or nail treatment products which generally comprise about 1–40% film former, 10–50% resin and 10–70% solvent, in addition to the usual plasticizers, pigments, and wetting agents.

The invention is also directed to pharmaceutical compositions comprising pharmaceutically effective amounts of extensin protein.

A pharmaceutically effective amount in accordance with the invention means about 0.01–30% of extensin protein, with 0.1–10% preferred, and 0.5–5% most preferred. The extensin proteins may be incorporated into suitable pharmaceutical vehicles such as lotions, creams, ointments, gels, or solutions. Suitable ointments are hydrophilic ointments (USP) or petrolatum and cosmetically effective amounts of extensin protein are incorporated into the ointment for topical application to skin. Suitable lotions and creams are as mentioned previously for cosmetic compositions. Solutions are made by mixing solutions of extensin protein in deionized water for application to human skin. Gels are made by mixing 1–90% water with a suitable polymer.

Suitable humectants for use in the cosmetic compositions of the invention include glycerin, propylene glycol, butylene glycol, urea, sorbitol, sodium PCA, gelatin, polyethylene glycols, sodium lactate, hyaluronic acid, and so on.

Suitable emollients include glyceryl stearate, cetyl alcohol, stearyl alcohol, isopropyl stearate, stearyl alcohol, stearyl stearate, isopropyl stearate, stearic acid, isobutyl palmitate, isocetyl stearate, oleyl alcohol, sebacates, myristates, palmitates, squalenes, glyceryl monooleate, oleic acids, lanolin, acetylated lanolin alcohols, petrolatum, mineral oils, palmitic acids, isostearyl neopentanoate, etc.

A variety of surfactants may be used in the compositions of the invention including amphoteric, anionic, cationic or nonionic surfactants. Suitable amphoteric surfactants include imidazolines, betaines, and amino acid salts. Suitable anionic surfactants include fatty acid soaps, salts of higher alkyl sulfates, n-acyl sarcosinates, salts of phosphates, sulfosuccinate salts, alkyl benzene sulfonates, salts of N-acyl glutamate, polyoxyethylene alkyl ether carboxylic acids, and so on. Cationic surfactants include alkyl trimethyl ammonium salts, alkyl pyridinium salts, alkyl quaternary ammonium salts, pelyamine fatty acid derivatives, etc. Nonionic surfactants include lipophilics such as sorbitan fatty acid esters, glycerol fatty acids, propylene glycol fatty acid esters; hydrophilics such as polyoxyethylene sorbitan fatty acid esters, polyoxyethylene glycerol fatty acid esters, polyoxyethylene fatty acid esters, polyoxyethylene alkyl ethers, pluronics, polyoxyethylene alkyl phenyl ethers, polyoxyethylene propylene glycol fatty acid esters, and so on.

Suitable pigments include organic and inorganic pigments such as talc, mica, titanium dioxide, titanated mica, iron oxides, ultramarines, chromium oxides, carmine, D&C and FD&C colors and lakes, ferric and ferrous oxides, and so on.

Suitable preservatives include imidazolidinyl urea, the parabens, quaternium 15, benzyl alcohol, phenoxyethanol and so on.

Suitable waxes include beeswax, carnauba, ceresin, microcrystalline, lanolin, paraffin, ozokerite, lanolin alcohol, acetylated lanolin, candelilla, cetyl alcohol, cocoa butter, petrolatum, hydrogenated castor oil, spermaceti, bran wax, capok wax, bayberry, etc.

The invention is also directed to a method for moisturizing and forming a film on human skin, nails, or hair comprising applying to the surface an effective amount of extensin protein. An effective amount of extensin is about 0.01–30% by weight. The extensin protein may be applied directly to the surface in a solution form, or it may be incorporated into the cosmetic or pharmaceutical compositions mentioned herein. The extensin protein or protein containing composition may be applied to the surface once or twice a day or as necessary. For example, if the extensin protein is incorporated into a facial moisturizer, usually one to two applications of moisturizer per day will provide a beneficial effect. If the extensin proteins are incorporated into shampoos or hair conditioners, usually application once a day or every other day will be sufficient to provide a beneficial effect. When extensins are incorporated into makeups, blushes, or eyeshadows, they provide a treatment effect to the skin when applied once a day or whenever makeup is worn. If incorporated into nail treatment products or nail enamels, consistent usage in a nail care regimen (i.e. once or twice a week) will provide beneficial results.

The invention will be further described in connection with the following examples which are set forth for the purposes of illustration only.

EXAMPLE 1

Bean seeds, (Phaseolus Vulgaris) or carrots (Daucus carota) are purchased from local gardening stores and the seeds germinated on moist filter paper in the dark. Germinated seeds are then planted in large window boxes or in gardens. Young plants are grown and then the hypocotyl and roots harvested and homogenized in 50 mM potassium phosphate buffer pH 6, 1 mM dithiothreitol (DTT), 0.1 mM phenyl methylsulfonyl fluoride and 2 mM ascorbate in an Osterizer (Waring) blender. The homogenate was diluted with 10 mM calcium chloride and centrifuged at 1000×G. Pellets were extracted again in 100 mM calcium chloride and recentrifuged. The supernatants were combined and dialyzed to remove excess salt. The result was a crude extensin extract suitable for incorporation into cosmetics or pharmaceuticals.

EXAMPLE 2

Small tomato plants are obtained from local gardening stores and acclimated to outdoor gardens. After two weeks small amounts of plant tissue are cut off and frozen in liquid nitrogen until a sufficient amount is collected (approximately 100 grams of wet tissue). Crude homogenates are made and extracted with 75 mM aluminum chloride.

EXAMPLE 3

Small pieces of potato are rooted by exposing the pieces to water containing 35 mM sodium azide, 0.5% ferulic acid, 0.05% curcumin, 0 1% carnosine, or 0.05% extract from spinach, gingo bilboa, or ginseng. The root systems formed are harvested and homogenized in 50–100 mM calcium chloride or 150 mM sodium chloride.

EXAMPLE 4

Pea seeds (Pisum sativum) are germinated and the epicotyl and root sections were dissected and extracted in a loosely stoppered flask at 70° C. with 0.12% v/v acetic acid and 0.3% sodium chlorite for 30 minutes under a nitrogen blanket. After cooling the solution was filtered through coarse glass wool and the residue washed five times with distilled water. Nitrogen is bubbled through the filtrate to remove any extraneous chlorine dioxide. The resulting homogenate is dialyzed to yield a crude extensin protein preparation.

EXAMPLE 5

An extensin containing oil in water moisturizing lotion is made as follows:

|  | w/w % |
| --- | --- |
| Glyceryl stearate | 3.0 |
| PPG-10 lanolin ether | 0.5 |
| Mineral oil | 6.3 |
| Lanolin alcohol | 0.7 |
| Oleic acid | 2.7 |
| Isocetyl stearate | 10.0 |
| Triethanolamine | 1.3 |
| Carbomer 941 | 0.1 |
| Glycerin | 4.0 |
| Preservative | 0.4 |
| Extensin solution from carrots[1] | 5.0 |
| Hydrolyzed extensin polypeptides[2] | 5.0 |

| | w/w % |
|---|---|
| Water | qs 100.00 |

[1] 5% solution
[2] 5% peptide solids, "Vegagen", Centerchem, Inc., Stamford, CT

EXAMPLE 6

An oil in water moisturizing cream was made as follows:

| | w/w % |
|---|---|
| Glyceryl stearate | 5.0 |
| Cetyl alcohol | 2.0 |
| Stearyl alcohol | 2.0 |
| Isopropyl stearate | 4.0 |
| Mineral oil | 12.0 |
| Polysorbate 60 | 1.0 |
| Glycerin | 8.0 |
| Xanthan gum | 0.25 |
| Preservative | 0.6 |
| Extensin solution from carrots[1] | 5.0 |
| Hydrolyzed extensin polypeptides from carrots[2] | 5.0 |
| Water | qs 100.00 |

[1] 5% solution
[2] Vegegen, Centerchem, Inc., Stamford, CT

EXAMPLE 7

An oil/water cream makeup was made as follows:

| | w/w % |
|---|---|
| Octyldodecyl stearyl stearate | 4.0 |
| Isocetylstearate | 1.0 |
| Glyceryl stearate | 6.0 |
| Isostearic acid | 2.0 |
| Stearic acid | 1.0 |
| Ceteth 10 | 1.0 |
| Cyclomethicone | 12.0 |
| Stearyl alcohol | 1.5 |
| Nonionic surfactant mixture[1] | 1.0 |
| Binders and thickeners | 1.7 |
| Titanium dioxide | 8.0 |
| Iron oxide | 2.0 |
| Propylene glycol | 3.0 |
| Triethanolamine | 1.5 |
| Preservatives | 0.55 |
| Extensin solution from tomato[2] | 1.0 |
| Water | qs 100.00 |

[1] lecithin, polysorbate 20, sorbitanlaurate
[2] 1.5% solution

EXAMPLE 9

A water/oil pigment emulsion makeup was made as follows:

| | w/w % | |
|---|---|---|
| Cyclomethicone | 22.6 | 12.0 |
| Dimethicone | — | 5.0 |
| Surfactant | 16.0 | 20.0 |
| Laureth 7 | 0.5 | — |
| Laureth 9 | — | — |
| Bentone gellant | 5.0 | — |
| Iron oxides | 3.1 | 2.4 |
| Titanium dioxide | 12.0 | 8.5 |
| Talc | 4.5 | 3.3 |
| Sodium chloride | 2.0 | 2.0 |
| Propylene glycol | 6.0 | 8.0 |
| Preservative | 0.5 | 0.5 |
| Extensin solution from potato | 0.5 | 0.5 |
| Water | qs 100.0 | |

EXAMPLE 10

A water/oil pigment emulsion eyeshadow was made as follows:

| | w/w % |
|---|---|
| Cyclomethicone | 2.0 |
| Dimethicone | 5.0 |
| Surfactant | 20.0 |
| Peg-7 $C_{12-15}$ ether | 0.5 |
| Chromium oxide | 6.2 |
| Ultramarine blue | 4.0 |
| Titanium dioxide coated mica | 6.0 |
| Sodium chloride | 2.0 |
| Propylene glycol | 8.0 |
| Preservatives | 0.3 |
| Extensin solution from potato[1] | 0.5 |
| Water | qs 100.0 |

[1] 1% solution

EXAMPLE 11

A protein shampoo was made as follows:

| | w/w % |
|---|---|
| Ammonium lauryl sulfate | 10.0 |
| Cocamide diethanolamine | 4.0 |
| Cocamidopropyl betaine | 4.0 |
| Ammonium chloride | 0.8 |
| Citric acid | 0.1 |
| Extensin solution from corn (1%) | 1.0 |
| Water | qs 100.0 |

EXAMPLE 12

A creme rinse hair conditioner was made as follows:

| | w/w % |
|---|---|
| Stearalkonium chloride | 2.0 |
| Cetyl alcohol | 1.0 |
| Stearyl alcohol | 0.5 |
| Ceteareth 20 | 2.0 |
| Xanthan gum | 0.5 |
| citric acid | 0.3 |
| Dimethicone | 0.2 |
| Extensin solution from corn (1%) | 0.2 |
| Water | qs 100.0 |

EXAMPLE 13

A variety of extensin containing personal care products are made as follows:

| | A | B | C | D |
|---|---|---|---|---|
| | | w/w % | | |
| Mineral oil | 20.0 | — | — | — |
| Beeswax | 2.0 | — | — | — |
| Polysorbate 40 | 8.0 | — | — | — |
| Polysorbate 20 | — | — | 1.0 | — |
| PEG 20 sorbitan beeswax | 2.0 | — | — | — |
| Stearic acid | 10.0 | — | — | — |
| Petrolatum | 4.0 | — | — | — |
| Sorbitol | 5.0 | — | — | — |
| Ethyl alcohol | — | 50.0 | 50.0 | 50.0 |

-continued

|  | A | B | C | D |
|---|---|---|---|---|
|  |  | w/w % |  |  |
| Menthol | — | 0.05 | — | 0.1 |
| Carbomer 940 | — | 0.75 | — | — |
| Triethanolamine | — | 0.75 | — | — |
| Polysorbate 80/acetyllated lanolin alcohol/cetyl acetate | — | 3.0 | — | — |
| Citric acid | — | — | — | 2.0 |
| Glycerol | — | — | — | 2.5 |
| Perfume | qs | 8.0 | 8.0 | 0.5 |
| Preservative | qs | — | — | — |
| Extensin solution from sycamore | 0.5 | 0.1 | 0.1 | 0.1 |
| Water (qs 100) |  |  |  |  |

A is a cleansing cream, B is a clear fragrance, C is a toner, D is an after shave.

EXAMPLE 14

Two nail enamel preparations were made as follows:

|  | w/w % | |
|---|---|---|
|  | A | B |
| Beeswax | 12.0 | — |
| Lanolin, anhydrous | 15.0 | — |
| Cocoa butter | 8.0 | — |
| Cetyl alcohol | 3.0 | — |
| Cholesterol | 1.0 | — |
| Mineral oil | 30.0 | — |
| Extensin solution from carrots (0.2%) | 5.0 | 0.5 |
| Preservative | qs | — |
| Perfume | qs | — |
| Water | qs 100 | — |
| Nitrocellulose | — | 15.00 |
| Toluene sulfonamide | — | 7.5 |
| Dibutyl phthalate | — | 3.75 |
| Butyl acetate | — | 29.35 |
| Ethyl alcohol | — | 6.4 |
| Butyl alcohol | — | 1.1 |
| Toluene | — | 36.40 |

EXAMPLE 15

Five dry skinned human subjects were tested to compare the film forming properties of substantially intact extensin and intact animal collagen. Aqueous solutions of intact extensin and intact animal collagen were prepared at 1% and 0.3% concentrations. Approximately 0.12 grams of each sample was applied to an area about 5 cm. in diameter on the skin on the back of each subject. The applications were allowed to dry for approximately 10 minutes. None of the subjects were told the composition of the solutions. Each of the five subjects ranked the skin treated with animal collagen as less esthetic than the extensin-treated skin. Each of the five subjects stated that the animal collagen treated skin was "draggy" and "tacky" and the film was described as "brittle" and subject to "rolling" (an indication of poor adhesion). All five subjects stated that the extensin treated skin was smoother, more moisturized, and the film was described as more flexible and more natural.

To rule out possible bias, a cross over experiment was conducted on a second day. The same solutions were applied to the same five subjects in accordance with the foregoing, except that the sites were switched. The subjects were then asked to evaluate the sites. All five subjects preferred the extensin treated skin regardless of application site. The subjects stated that the extensin treated skin was consistently smoother, more moist, and the film more flexible and natural. This indicates that intact extensin forms a more flexible, better adhering film than animal collagen and leaves skin smoother and more moisturized.

EXAMPLE 16

In order to compare moisturizing and film forming effects of hydrolyzed extensin (100–1500 daltons) with substantially intact extensin, four dry skinned individuals were tested. A 6% solution of hydrolyzed extensin of 1000–1500 daltons (Centerchem, Stamford Conn.) was prepared. Approximately 0.04 grams of product was applied to an area 5 cm. in diameter on the skin surface of each subject and allowed to dry approximately 10 minutes. None of the four subjects was able to detect any film on the skin surface although all reported a tacky residue. Conclusion: Hydrolyzed extensin, even when used at concentrations at least seven times greater than the intact extensin, does not form a film on skin.

While the invention has been described in connection with the preferred embodiment it is not intended to limit the scope of the invention to the particular form set forth, but, on the contrary, it is intended to cover such alternatives, modifications, and equivalents as may be included within the spirit and scope of the invention as defined by the appended claims.

We claim:

1. A cosmetic composition for external application to human skin, nails, or hair for the purpose of beautifying, coloring, conditioning, or protecting the body surface, said cosmetic composition selected from the group consisting of a cream, lotion, gel, makeup, eyeshadow, blush, shampoo, hair conditioner, cleanser, toner, aftershave, fragrance, nail enamel, or nail treatment product and comprising 0.001–30% of a non-hydrolyzed soluble precursor form of extensin extracted from plant species in the growth phase by salt extraction of extensin fractions from plant cell suspensions or explant homogenates, which extensin precursor has a molecular weight of 100.000 to 150,000 daltons.

2. The composition of claim 1 comprising 0.1–10% by weight of extensin precursor.

3. The composition of claim 1 which is a water and oil emulsion lotion containing 20–80% oil and 10–80% water.

4. The composition of claim 1 which is a water and oil emulsion cream comprising 20–70% water and 30–70% oil.

5. The composition of claim 1 which is a water and oil emulsion makeup comprising 5–70% oil, 10–95% water, and 5–40% pigment.

6. The composition of claim 1 which is an eyeshadow comprising 5–40% pigment, 1–50% oil, and 1–20% wax.

7. The composition of claim 1 which is a shampoo composition comprising 1–40% surfactant and 10–90% water.

8. The composition of claim 1 which is a hair conditioner comprising 30–95% water and 0.5–30% conditioning ingredients.

9. The composition of claim 1 which is a toner composition comprising 10–70% alcohol.

10. The composition of claim 1 which is a nail enamel comprising 1–40% film former, 10–50% resin, and 10–70% solvent.

11. The composition of claim 1 which is a gel.

12. The composition of claim 1 wherein the extensin exists in the form of dimers.

13. The composition of claim 2 comprising 0.5–5% extensin.

14. The composition of claim 1 wherein the salt extraction is conducted with a metallic salt solution wherein the metal is aluminum, calcium, sodium or mixtures thereof, or with lapyrium chloride.

15. The composition of claim 14 wherein the salt solution is selected from the group consisting of aluminum chloride, calcium chloride, lapyrium chloride, sodium chloride, and mixtures thereof.

16. The composition of claim 14 wherein the extensin is extracted from plant cell suspensions.

17. The composition of claim 16 wherein the extensin is subsequently purified by acid precipitation of contaminants.

* * * * *

REEXAMINATION CERTIFICATE (3439th)
United States Patent [19]
Wolf et al.

[11] B1 5,443,855
[45] Certificate Issued Feb. 10, 1998

[54] COSMETICS AND PHARMACEUTICALS CONTAINING EXTENSINS AND RELATED METHODS

[75] Inventors: Barbara Wolf, Scarsdale; Marlene Tietjen, New York, both of N.Y.

[73] Assignee: Revlon Consumer Products Corporation

Reexamination Request:
No. 90/004,175, Mar. 8, 1996

Reexamination Certificate for:
Patent No.: 5,443,855
Issued: Aug. 22, 1995
Appl. No.: 296,385
Filed: Aug. 26, 1994

Related U.S. Application Data

[63] Continuation of Ser. No. 27,996, Mar. 8, 1993, abandoned, which is a continuation-in-part of Ser. No. 933,130, Aug. 21, 1992, abandoned, which is a continuation of Ser. No. 761,574, Sep. 18, 1991, abandoned.

[51] Int. Cl.⁶ ............ A61K 7/00; A61K 7/02; A61K 7/04; A61K 7/075
[52] U.S. Cl. .......... 424/401; 424/61; 424/70.14; 424/73; 514/844; 514/845; 514/846; 514/847; 514/881; 514/937; 514/938; 514/944

[58] Field of Search ............ 424/401, 61, 70.14, 424/73; 514/844, 845, 846, 847, 881, 937, 938, 944

[56] References Cited

U.S. PATENT DOCUMENTS 4,507,279   3/1985   Okuyama .................. 424/63

FOREIGN PATENT DOCUMENTS 2148714   6/1985   United Kingdom .

OTHER PUBLICATIONS

Perserpio Cosmetic News II, #3 (1988).

Exhibit C, Marcet, Pedro, "Estensina*: Un Nuovo Concettoper Cosmetici Sicuri", Cosmetic News, 75, Nov.–Dec. 1990.

Exhibit D, Marcet, Pedro, "Extensin*: A New Concept For Safe Cosmetics", Cosmetic News 75, Nov–Dec. 1990. (English translation).

*Primary Examiner*—Gollamudi S. Kishore

[57] ABSTRACT

Cosmetic and pharmaceutical compositions containing effective amounts of substantially intact extensin proteins and the related methods.

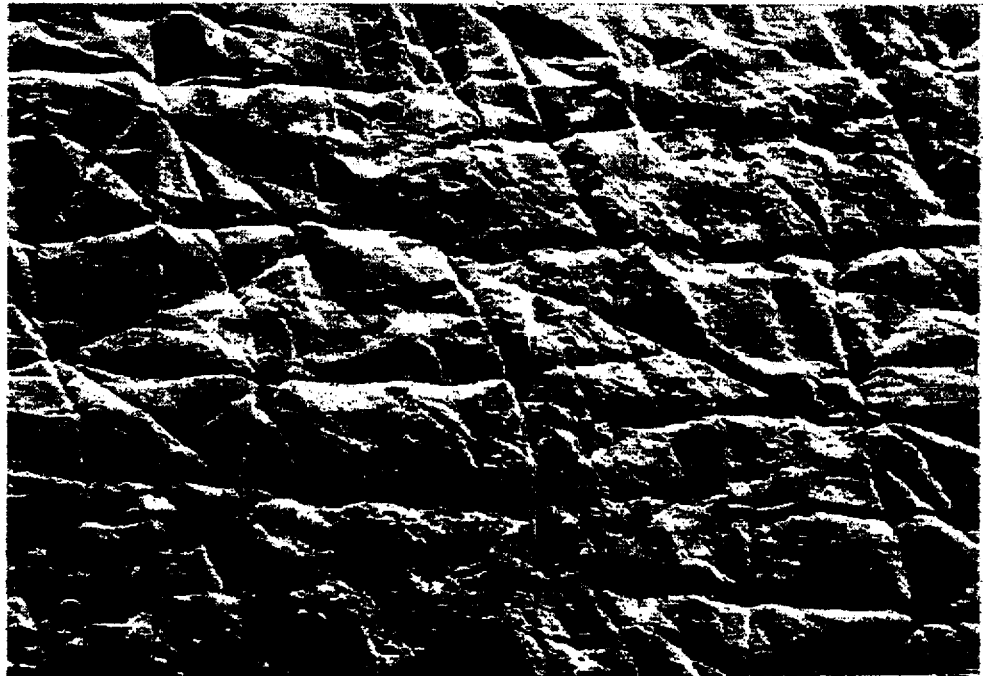

NO TREATMENT | TREATED

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–17 is confirmed.

New claim 18 is added and determined to be patentable.

*18. A cosmetic composition selected from the group consisting of:*

*(i) a cream which is a water and oil emulsion comprising 20–70% water and 30–70% oil,*

*(ii) a lotion which is a water and oil emulsion containing 20–80% oil and 10–80% water,*

*(iii) a water and oil emulsion makeup comprising 5–70% oil, 10–95% water, and 5–40% pigment,*

*(iv) an eyeshadow comprising 5–40% pigment, 1–50% oil, and 1–20% wax,*

*(v) a shampoo comprising 1–40% surfactant and 10–90% water,*

*(vi) a hair conditioner comprising 30–95% water and 0.5–30% conditioning ingredients,*

*(vii) a toner comprising 10–70% alcohol,*

*(viii) a nail enamel comprising 1–40% film former, 10–50% resin, and 10–70% solvent,*

*wherein the composition further comprises 0.001–30% of a non-hydrolyzed soluble precursor form of extensin extracted from plant species in the growth phase by salt extraction of extensin fractions from plant cell suspensions or explant homogenates, which extensin precursor has a molecular weight of 100,000 to 150,000 daltons.*

* * * * *